(12) United States Patent
Merboth et al.

(10) Patent No.: US 7,081,123 B2
(45) Date of Patent: Jul. 25, 2006

(54) BONE MARROW ASPIRATION INSTRUMENT

(75) Inventors: Barbara L. Merboth, Bridgewater, NJ (US); Adam Stephens, Norwalk, CT (US); Yukiko Naoi, New York, NY (US); Kazuna Tanaka, Cos Cob, CT (US); Jeffrey Kapec, Westport, CT (US)

(73) Assignee: Musculoskeletal Transplant Foundation, Edison, NJ (US)

( * ) Notice: Subject to any disclaimer, the term of this patent is extended or adjusted under 35 U.S.C. 154(b) by 0 days.

(21) Appl. No.: 10/173,425

(22) Filed: Jun. 18, 2002

(65) Prior Publication Data

US 2003/0233114 A1 Dec. 18, 2003

(51) Int. Cl.
*A61B 17/34* (2006.01)

(52) U.S. Cl. .............. 606/185; 606/167; 604/164.01; 600/565; 600/576

(58) Field of Classification Search ................ None
See application file for complete search history.

(56) References Cited

U.S. PATENT DOCUMENTS

| 4,356,828 | A |   | 11/1982 | Jamshidi |         |
|-----------|---|---|---------|----------|---------|
| 4,403,617 | A |   | 9/1983  | Tretinyak |        |
| 4,469,109 | A |   | 9/1984  | Mehl     |         |
| 4,793,363 | A | * | 12/1988 | Ausherman et al. | 600/567 |
| 4,838,282 | A |   | 6/1989  | Strasser et al. |   |
| 5,350,393 | A | * | 9/1994  | Yoon     | 606/185 |
| 5,490,521 | A | * | 2/1996  | Davis et al. | 600/458 |
| 5,538,009 | A | * | 7/1996  | Byrne et al. | 600/567 |
| 5,758,655 | A | * | 6/1998  | Como Rodriguez et al. | 600/562 |
| 5,807,275 | A | * | 9/1998  | Jamshidi | 600/567 |
| 5,807,277 | A | * | 9/1998  | Swaim    | 600/567 |
| 6,110,128 | A | * | 8/2000  | Andelin et al. | 600/566 |
| 6,306,053 | B1 | * | 10/2001 | Liechty, II | 473/583 |
| 6,312,394 | B1 | * | 11/2001 | Fleming, III | 600/567 |
| 6,613,018 | B1 | * | 9/2003  | Bagga et al. | 604/187 |
| 6,749,595 | B1 | * | 6/2004  | Murphy   | 604/500 |

FOREIGN PATENT DOCUMENTS

EP 0378095 * 3/1990 ................ 606/185

* cited by examiner

*Primary Examiner*—Glenn K. Dawson
(74) *Attorney, Agent, or Firm*—John S. Hale

(57) ABSTRACT

The cannula handle housing includes a recessed seat, wings extending outwardly from the recessed seat in the housing for engagement with a physician's hand and a stem which extends from said housing to hold a portion of a cannula The cannula has a distal sharpened end and a proximal end secured to a Luer lock. The stylet includes a longitudinal member having a sharp tip with the other end of the stylet formed with an anvil structure which is molded into a stylet cap. The stylet cap is a housing which includes a projection portion having a complimentary configuration to the recessed seat formed in said cannula housing for interlocking with the Luer lock of the cannula housing. The stylet inserts into the cannula and with a twist, locks about the Luer lock on the proximal end of the cannula.

20 Claims, 4 Drawing Sheets

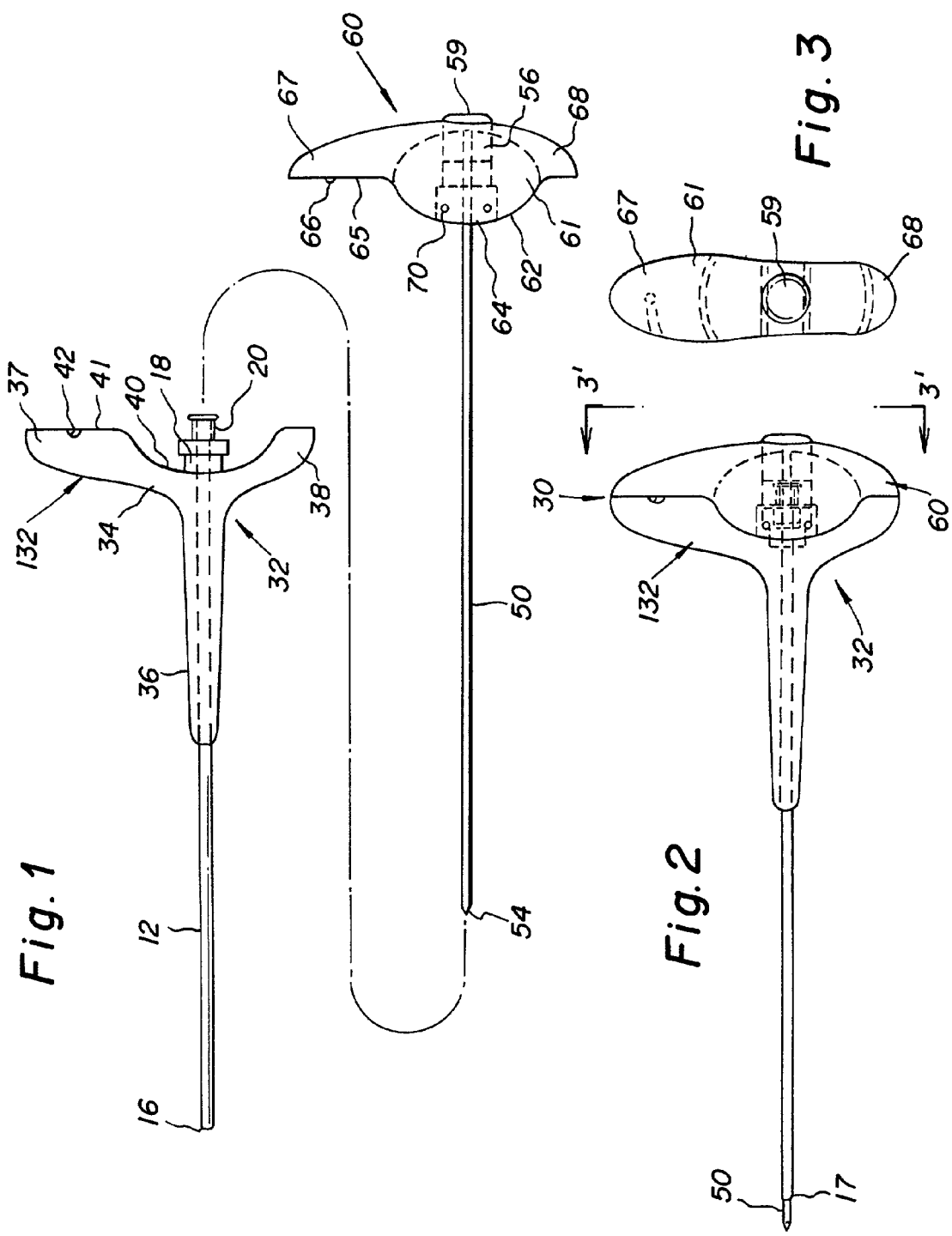

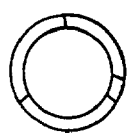
Fig. 6
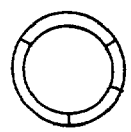
Fig. 8
Fig. 10
Fig. 12
Fig. 11
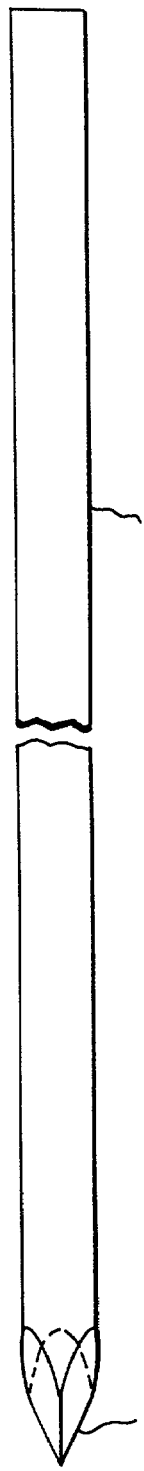
Fig. 13
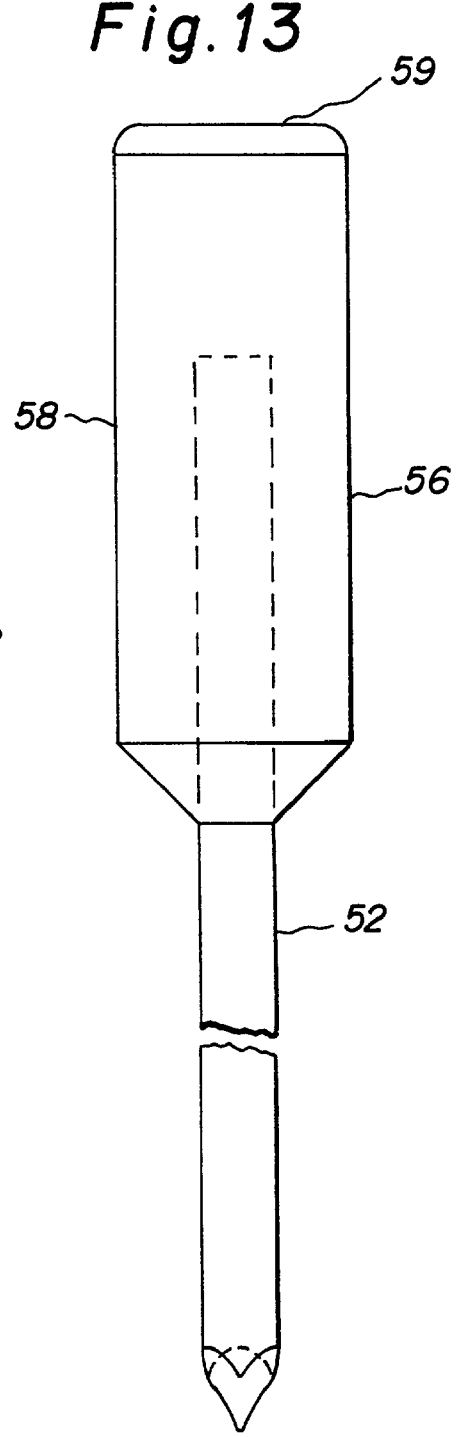

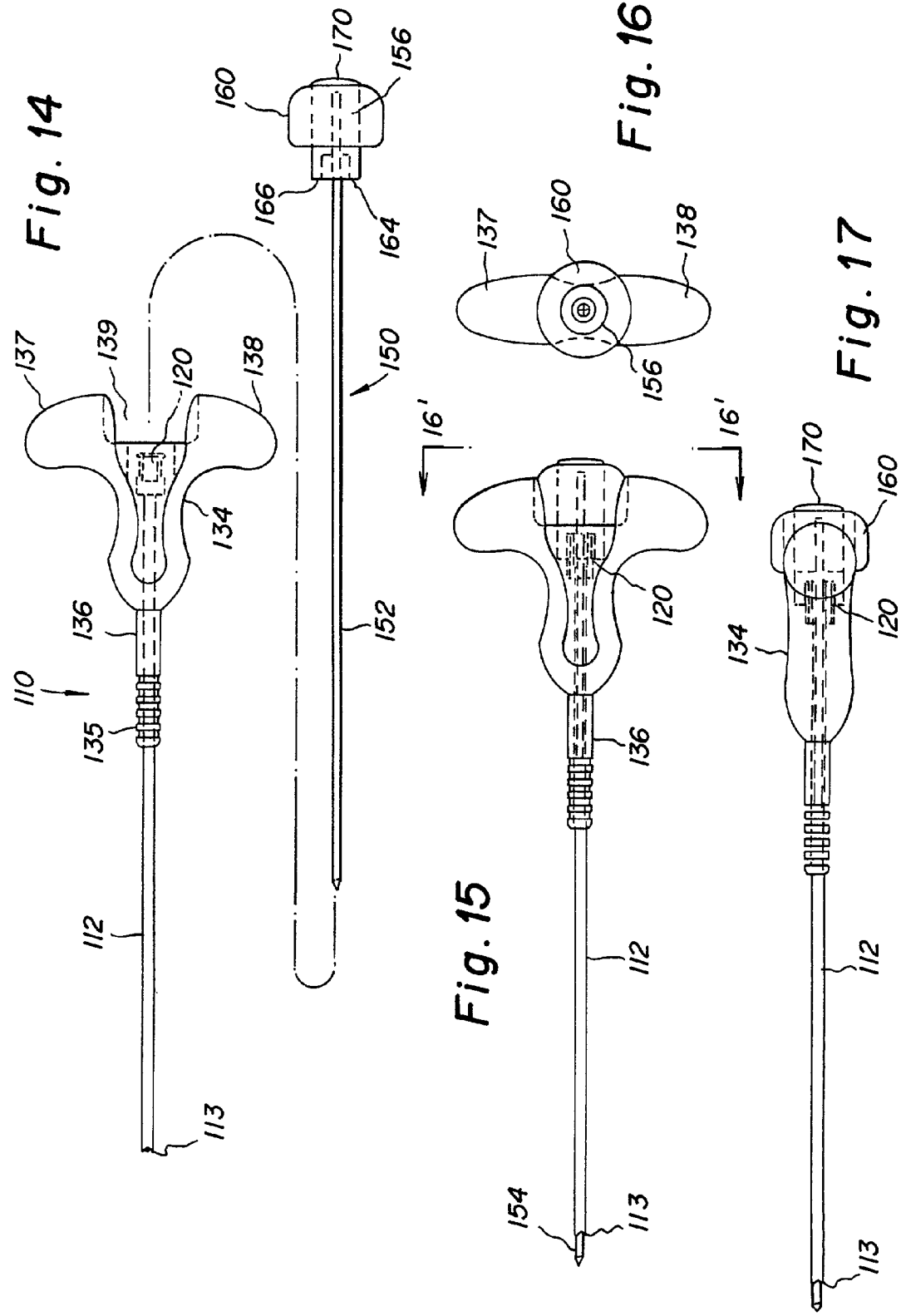

BONE MARROW ASPIRATION INSTRUMENT

RELATED APPLICATIONS

There are no related applications.

FIELD OF THE INVENTION

The present invention generally relates to a bone marrow aspiration instrument for gathering bone marrow for the repair and replacement of the various portions of the human skeletal system. The present invention is specifically directed to provide a bone marrow aspiration instrument having a cannula which extends from a handle and a stylet assembly including a striking anvil which extends through the handle and cannula. This instrument can be conveniently grasped by the physician or surgeon in the palm of the hand to provide secure control during insertion of the instrument into a human bone and subsequent withdrawal of bone marrow.

BACKGROUND OF THE INVENTION

The repair, as well as the replacement, of diseased and damaged human bone have been the subject of substantial research efforts over the past several decades. This research has yielded advances in the reconstruction of many areas of the human skeletal system As a result of these advances, bone replacements and repair are presently being undertaken in several areas including the restructuring of the craniofacial system, bone repair, spinal repair, the introduction of knee and hip joints and ligament replacement.

The biological mechanisms underlying the reconstruction and repair varies according to the type of bone implant selected. New bone can be formed by three basic mechanisms: osteogenesis, osteoconduction and osteoinduction. In osteogenic transplantation, viable osteoblasts and osteoclasts are moved from one body location to another where they establish centers of bone formation. Autograft tissue, cancerous bone and marrow grafts provide such viable cells. As a generalization, spongy cancerous bone permits rapid and usually complete reossification.

In the transplantation of large segments of allogenic banked bone, direct osteogenesis does not occur. In these cases, osteoconduction transpires—the dead bone acts as a scaffold for the ingrowth of blood vessels, followed by the resorption of the implant and deposition of new bone. This process is slow, sometimes requiring years to reunite a large segmental defect. As a generalization, cortical bone has high strength and undergoes osteoclastic digestion of the bone and revascularizes through pre-existing anatomical channels, a relatively slow process.

Osteoinduction is the phenotypic conversion of connective tissue into bone by an appropriate stimulus. As this concept implies, formation of bone can be induced at even non-skeletal sites. Osteoinduction is the preferred method of providing new bone growth as allografts of this type are typically incorporated into the host bone within several weeks. In contrast, some osteoconductive grafts have been found to be non-incorporated as long as one year after implantation.

In order to provide an environment suitable for osteoinduction, a material should be selected which is not only capable of inducing osteogenesis throughout its volume, but is also biocompatible, non-inflammatory, and possesses the ability to be ultimately resorbed by the body and replaced with new, natural bone. Demineralized bone is osteoinductive and when used in surgery by a physician is quite often mixed with marrow retrieved from the patient at the time of surgery.

In most bone marrow collecting procedures, multiple aspirations of bone marrow are required to enable enough bone marrow to be collected to perform a bone marrow transplant to the surgical site or be mixed with the osteoinductive material being used at the surgical site. Bone marrow density can and does vary from patient to patient and there is no uniform viscosity to bone marrow. Younger healthy patients often have denser thicker marrow. Usually thicker marrow is the result of more trabecula tissue present in the cavity. All of these bone marrow collecting procedures require that the bone be punctured in order to access the bone marrow within. Generally bone marrow aspiration is accessed via an open wound, most typically by exposing the iliac crest. In many instances, the instrument tip is difficult to fix into the bone as it skates over the curved hard irregular surface of the iliac crest. Thus, it is important to provide an instrument which enhances the ability of the user to easily puncture bone and obtain bone marrow with minimal trauma to the patient.

The bone marrow removal procedure is quite painful to the patient and requires much exertion and care by the physician in operating the instrument. Early problems with biopsy needles involved the sharpness of the cannula and trocar and the gripping means used so that the needle could be placed accurately and the bone could be penetrated quickly. U.S. Pat. No. 4,356,828, for example, discloses an improved finger gripping member and U.S. Pat. No. 4,403,617 discloses particular cutting edge configurations for the trocar and cannula. Developments in the gripping means of the trocar and cannula continued with emphasis being placed on the secure engagement of the trocar within the cannula and ease of use for the physician.

All bone marrow biopsy, aspiration and transplant needles or cannulas currently on the market have a handle with a cannula extending outwardly from the handle. The handle is used by the surgeon to apply force to the cannula as the cannula penetrates the bone. Such needles typically include a stylet with a sharpened tip which is inserted through the cannula and is used to initially penetrate the bone. The stylet also serves to occlude the cannula while the bone is penetrated, so that the marrow sample subsequently taken is free from bone chips. The stylet is then removed and bone marrow is withdrawn from the patient by manipulating the cannula to cause bone marrow to move into the interior of the cannula. In some cases a slight suction is applied to the cannula to hold the bone marrow specimen within the cannula as the device is removed from the patient or a syringe can be attached to the cannula to remove the bone marrow as is shown in U.S. Pat. No. 4,838,282.

Previous prior art biopsy or collection instruments have grips which do not really fit into the physician's hand to provide for positive gripping by the physician but have grips which are required to be engaged by the physician in a negative way making the process of biopsy or bone marrow collection uncomfortable to the physician/surgeon using the instrument. The handles of the bone marrow collection instrument must securely engage into the physician's or surgeon's palm for optimum control of the instrument during a biopsy or surgery and be easily grasped by the fingers of the user. It is also necessary that the stylet and cannula be engaged to each other during the surgical process for providing total control to the physician or surgeon.

Prior art needles have secured cannula tubes into the cannula housing in numerous ways providing increased manufacturing processes, resulting in an increased end cost to the patient.

The present invention overcomes the disadvantages of the prior art references by providing a bone marrow aspiration instrument having a winged cannula handle and detent locking between the stylet handle and cannula handle.

Bone marrow needles have traditionally been designed so that the needle is attached to the center of the handle. While many physicians feel comfortable with a centrally attached needle, it has been discovered that it may be easier to guide a needle with a user's index finger when the needle is not centrally located on the handle of the needle assembly. It has also recently been discovered that when an off-center device is used, it is important to insure that a physician's arm, wrist, and index finger are all generally in alignment with the cannula of the needle to provide enhanced control over the needle. Examples of such devices are described in U.S. Pat. No. 4,469,109.

Another disadvantage of most bone marrow instruments currently on the market is that when the stylet is removed from the cannula, the shape of the handle typically is materially changed. For example, the bone marrow needle assembly described in U.S. Pat. No. 4,838,282 involves removing approximately half of the handle assembly when the stylet is removed from the cannula. It is desirable to maintain substantially the original shape of the handle after the stylet has been removed to allow a physician to more easily manipulate the cannula within a patient's bone.

SUMMARY OF THE INVENTION

In a preferred embodiment of the invention the cannula handle has a body which is mounted to a cannula offset form the cannula axis. The proximal surface of the body defines a recess forming a saddle which receives a mating section of a stylet assembly. A Luer lock connected to the cannula extends outward from the saddle surface to receive a locking assembly carried by the stylet assembly. The off-center radius causes the handle to have a first major wing extension and a second minor wing extension on opposite sides of the cannula which provides a curved lower surface designed to be easily gripped by a user's fingers. Thus, when a user grips the handle, the user's index finger can be naturally applied to a stem extending from the handle housing opposite the saddle recess which surrounds the cannula to guide the cannula into a patient. A stylet is mounted in the cannula and a portion of the stylet handle is seated in the cannula handle saddle. The striking end of the stylet slightly extends from the stylet handle to allow direct force to be applied to the stylet tip.

It is an object of the invention to provide a bone marrow aspiration instrument having an ergonomically shaped offset handle to assist a physician in inserting a needle into a patient.

It is still another object of the invention to provide a bone marrow aspiration instrument having a handle design such that the shape of the handle allows the same to be easily used after the stylet has been removed.

It is yet another object of the invention, that the stylet is provided with a handle that is received within a saddle recess formed in the cannula handle with the stylet having a striking surface which extends beyond an upper surface of the stylet handle and provides direct transmission of force to the stylet.

It is a further object to provide a bone marrow instrument wherein an improved means is provided to prevent rotation and movement of the stylet relative to the cannula.

It is still another object of the invention to provide a bone marrow aspiration instrument having wing-shaped handles facilitating gripping and engagement by the physician or surgeon user.

These and other objects, advantages, and novel features of the present invention will become apparent when considered with the teachings contained in the detailed disclosure which along with the accompanying drawings constitute a part of this specification and illustrate embodiments of the invention which together with the description serve to explain the principles of the invention

BRIEF DESCRIPTION OF THE DRAWINGS

FIG. 1 is an exploded side elevational view of the inventive bone marrow aspiration instrument;

FIG. 2 is an assembled elevational view of the bone marrow aspiration instrument of FIG. 1;

FIG. 3 is an end view of the bone marrow aspiration instrument of FIG. 2 taken from directional line 3'—3';

FIG. 6 is an end view of the cannula of FIG. 5;

FIG. 8 is an end view of the cannula of FIG. 7;

FIG. 10 is an end view of the stylet tip of FIG. 9;

FIG. 11 is an enlarged broken side view of another stylet embodiment which can be used with the bone marrow aspiration instrument;

FIG. 12 is an end view of the stylet tip of FIG. 11;

FIG. 13 is an enlarged broken view of the stylet of FIG. 9 with a strike anvil on the proximal end.

FIG. 14 is an exploded side elevational view of another embodiment of the inventive bone marrow aspiration instrument;

FIG. 15 is an assembled elevational view of the bone marrow aspiration instrument shown in FIG. 14;

FIG. 16 is an end view of the bone marrow aspiration instrument of FIG. 15 taken in the direction of line 16'—16'; and FIG. 17 is atop plan view of the bone marrow aspiration instrument shown in FIG. 15.

DETAILED DESCRIPTION OF THE INVENTION

While the present invention and best mode of the invention is shown in FIGS. 1 through 3 and will be described in connection with certain preferred embodiments, it is not intended that the present invention be so limited. On the contrary, it is intended to cover all alternatives, modifications, and equivalent arrangements as may be included within the spirit and scope of the invention as defined by the appended claims.

Figure 4:
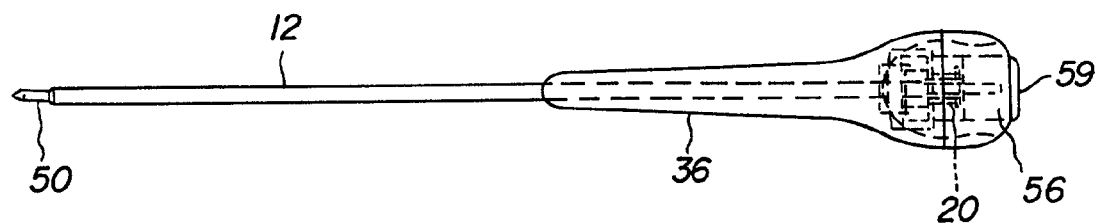
FIG. 4 is a top plan view of the bone marrow aspiration instrument of FIG. 2.
Figure 5:
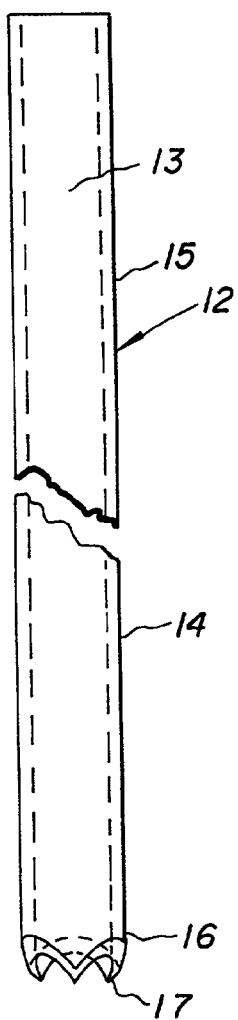
FIG. 5 is an enlarged broken side view of a cannula used in the bone marrow aspiration instrument.
Figure 7:
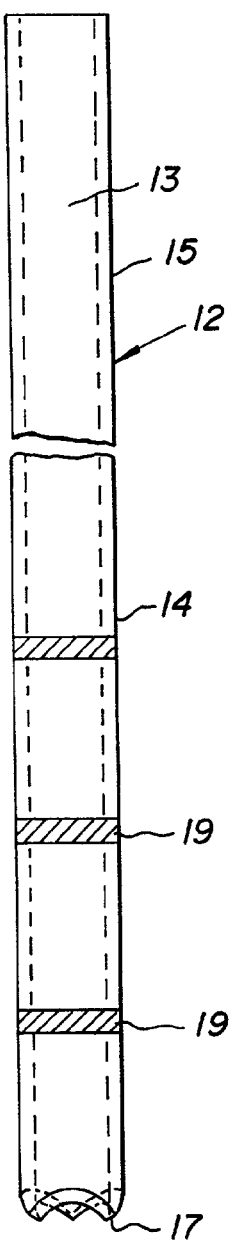
FIG. 7 is an enlarged broken side view of another cannula used in the bone marrow aspiration instrument.

In the present invention the bone marrow aspiration instrument 10 includes a hollow cannula 12 having a shaft 14 with an open sharpened distal end 16 having a scalloped sharpened edge 17 and a proximal end 18 which is secured to a luer lock 20. The cannula 12 preferably has a diameter running from 8 gauge to 14 gauge with an OD ranging from about 0.1660' to about 0.0820' and an ID ranging from about 0.1540' to about 0.0610' and is constructed of 304 alloy stainless steel with a ground straight bevel cut end as shown in FIGS. 7 and 8 or a radius cut end as shown in FIGS. 5 and 6. The cannula lumen 13 and cannula outer shaft surface 15 is preferably completely coated from the proximal to distal end with a surface modified lubricant coating which reduces the coefficient of friction such as silicon, TEFLON or a medical lubricant such as MH (ground sapphire). This improves the lubricity of the lumen and reduces the resistance to draw the aspirate through the lumen thus reducing any trauma imposed on the marrow cells. The lubricity of the outer shaft surface is also improved allowing easier entry and travel through the bone material. The exterior surface 15 of the cannula 12 can also be laser etched with bands 19 as shown in FIG. 8 to enable the surgeon to gauge the depth of penetration of the instrument.

The proximal end portion of cannula shaft 12 and associated Luer lock 20 which is mounted thereto are mounted in the cannula handle section 32 of handle assembly 30. The handle assembly 30 is composed of two interlocking sections, gripping cannula handle section 32 and stylet handle section 60. The handle sections as well as any other parts coming into fluid contact, are preferably formed from a polystyrene terpolymer of acrylonitrile, butadiene and styrene (ABS) or, alternatively, a polycarbonate polymer. The cannula handle section 32 has a curved body 34 eccentrically mounted on the cannula 12 with a stem extension 36 extending away from the curved body 34 surrounding the cannula 12 on its proximal surface. This stem extension 36 of the handle stiffens the cannula 12 so that there is less flexing of the cannula 12 when it is penetrating through the cortical bone. Flexing is not desirable because it absorbs some of the force applied to penetrate the cortical bone. A stiff shaft also transmits more tactile feedback into the hands of the surgeon. Another desirable aspect of the stem extension 36 is that it provides a place for the surgeon to position and rest his or her index finger. This pointing posture provides enhanced control and precision placement of the needle or stylet tip.

The handle geometry is ergonomically contoured to fit the hand and the shape is specifically tailored for the twisting and controlled removal of the needle from cortical bone. The distal tip of the handle is extended beyond the grip portion of the handle. The contour provides an optimum position for the fingers to hold and stabilize the handle while tapping the stylet striking surface with a hammer. The curved body 34 has a major wing portion 37 and a minor wing portion 38 which serve to allow grasping by the little finger of the hand on the underside of the minor wing portion 38 and the several fingers of the hand on the underside of the major wing portion 37. The contours of the handle section 32 are designed to provide a stable balanced grip on the handle. The cannula handle section 32 is designed to enhance grasping, turning, manipulation and twisting of the cannula 12 and stylet 50. The body 34 defines a arcuate recessed saddle or seat 40 which seats and holds a correspondingly shaped portion 62 of the stylet handle 60 in a mating relationship. Luer lock 20 secured to cannula 12 extends upward and away from the outer surface of seat 40. The upper surface of the wings of body 34 on either side of the recessed seat 40 has a planar surface 41 with a small locking depression 42 cut therein on the major wing portion planar upper surface to receive a locking nipple 66 extending from planar surface 65 of the stylet handle 60.

Figure 9:
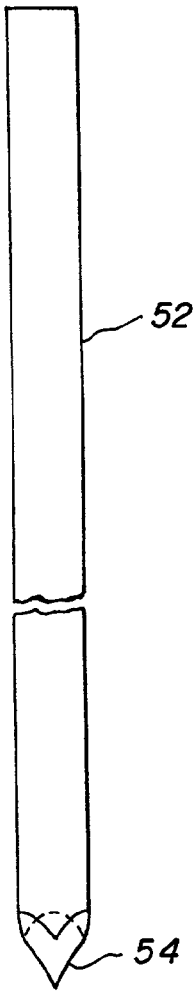
FIG. 9 is an enlarged broken side view of a stylet used in the bone marrow aspiration instrument.

A stylet 50 with a solid cylindrical shaft 52 is mounted in the cannula 12 so that it's triangular pointed tip 54 slightly protrudes from the distal end of the cannula 12 past the scalloped edges 17 as can be seen in FIG. 2. Alternatively the tip 54 can be positioned flush with the distal end of the cannula 12 adjacent the scalloped edges. A striker or anvil end member 56 is secured with the other end of the stylet 50 and is mounted in the stylet upper handle body 61, so that it has an exposed striking surface 59 slightly extending above the body surface. The stylet point is very sharp and formed from a harder grade of stainless alloy such as 420 alloy stainless steel which tends to maintain its sharp point and edges so that it will set into the bone with just a very slight force applied to the strike anvil 56. The stylet point or tip 54 can have a straight cut as seen in FIGS. 11 and 12 or a straight bevel cut as seen in FIGS. 9 and 10. The center of the striking end 59 of the strike anvil 56 is in line with the axis of the stylet 50. The strike anvil 56 is machined from stainless steel and has a cylindrical body 58 machined at one end 45 degrees as is more clearly shown in FIG. 13 to form a taper leading to the cylindrical shaft 52 with the other end of the strike anvil 56 forming a flat surface 59 which transmits the force from the hammer in a precise and controlled manner. All of the force is thus transmitted to the stylet tip 54 with none of the force being absorbed into the handle structure. The anvil 56 is mounted in the handle section 60 and is slightly raised or extended beyond the outer surface of the handle body 61 to allow easier striking force to be applied.

The stylet handle section 60 has the stylet 50 secured thereto and its body 61 has major and minor wings 67 and 68, respectfully, which can be respectively positioned adjacent to the lower wings 37 and 38 of the cannula handle. The body 61 has a curved seating projection 62 having a complementary dimension to fit into and mate with seat 40. Projection 62 defines a central cylindrical chamber 64 which can receive the Luer lock 20 of the lower gripping handle 32. The portions of the underside surface of the body 61 on opposite sides of projection 62 have a planar surface 65 allowing it to set flush against planar surface 41 of the corresponding structure of the lower cannula handle section 32. The major wing portion 67 of the body defines locking nipple 66 which fits in locking depression 42 on the upper planar surface of the lower cannula handle 32 to keep the two handle sections in a fixed relationship when the device is being used. Two parallel locking pins or rods 70 are mounted to the curved projection 62 on opposite sides of the cylindrical chamber 64. The parallel orientation of the rods 70 allows insertion of the same over the Luer lock 20 and rotation of the body 61 90° degrees to lock the handle assembly 30 in place, with the respective major and minor wing portions of the two handle sections 32 and 60 being positioned adjacent each other. The stylet can be removed by twisting the stylet handle section 60 in relation to the lower cannula handle section 32 to disengage the rods 70 from the Luer lock 20 allowing the stylet to be removed from the cannula 12 and a standard syringe (not shown) to be attached to the Luer lock 20 for the purpose of withdrawing bone marrow.

An alternate instrument embodiment 10 is shown in FIGS. 14–17. In this embodiment a cannula handle 132 has an outwardly curved body 134 mounted on the cannula 112 with a stem extension 136 extending away from the curved body 134 surrounding the proximal end of the cannula 112. This stem extension 136 of the handle stiffens the cannula 112 so that there is less flexing of the cannula 112 when it is penetrating through the cortical bone for the reasons previously mentioned. The stem 136 is also provided with annular gripping rings 135 cut into the body of the stem to provide a better gripping surface for the surgeon. The curved body 134 has two extending substantially identically formed curved wings 137 and 138 which serve to allow grasping by the fingers of the surgeon's hand on the underside of the wings. The contours of the section are designed to provide a stable balanced grip on the handle.

The body 134, stem 136 and the upper lateral end wings 137 and 138 are preferably formed from a single molded piece of plastic having a composition the same as that previously disclosed above in the preferred embodiment. A Luer lock 120 or associated cannula hub is molded to the proximal end of cannula 112 and serves to secure the cannula 112 to the stylet 150 in a conventional Luer lock grip. The Luer lock 120 extends upwardly into a recess 139 defined between the wings 137 and 138.

The stylet 150 has a shaft 152 with the distal tip 154 of the stylet extending beyond the distal end 113 of cannula 112 when it is fully inserted in the cannula. The stylet can have the same point structure as shown in FIGS. 9–12. A stylet handle or knob 160 is secured to the other end of the stylet to the stylet anvil member 156. The anvil member 156 is constructed with a cylindrical body which sits in the recess 139 between the wings and a cylindrical locking assembly 164 which extends over the Luer lock 120. The locking assembly 164 defines a central chamber 166 and locking pins (not shown) which fit over the Luer lock 120 extending between the wings 137 and 138. The wings shelter between them the Luer lock 120 which is molded onto the cannula. When the stylet knob 160 has been received by the cannula Luer lock the detent ribs or pins overlap the shouldered projection of the Luer lock to enclose the Luer lock. The upper surface of the knob body is provided with a striking surface 170 which can be a tapped with a hammer to drive the stylet into the bone. The stylet should be very stiff and have a very sharp edge with a large diameter cannula to reduce the resistance of the marrow draw.

In the operation of the instrument of this invention, the instrument is grasped in the physician's hand and is introduced through an incision, through the soft tissue toward and into contact with bone structure being tapped, usually the posterior iliac spine. Gentle tapping of the anvil should set the stylet and cannula into the bone so that it does not skid or walk when it is implanted on the iliac crest as some patients have dense bone which makes it difficult to initially pierce. The surgeon slowly advances the stylet and cannula through the cortical bone, millimeter by millimeter by tapping gently on the stylet striking surface. Tapping on the top of a molded plastic handle which attached to the aspiration needle reduces the tactile feedback. It is thus better to have a metal striking surface which would provides a much better striking surface. The striking surface of the present invention allows transmittal of the force to the stylet tip more efficiently and provides precise tactile and audible feedback. Pushing or drilling into the pelvic bone with a tool always presents the possibility of trauma and in older patients that may have a thin cortical bone, it is possible to accidently puncture a structure if the instrument passes through quickly. The surgeon is thus able to feel passage through cortical bone which is an important characteristic of the present invention. The cannula and stylet are advanced into the marrow cavity. Once the marrow cavity has been reached, the stylet is removed. Deep penetration of the cannula into the marrow cavity does not product quality aspirate as deeper penetration generally will produce a thinner aspirate. The surgeon then rotates the tip of the cannula to help draw out aspirate. A syringe plunger is attached to the Luer connector on the cannula handle and bone marrow is withdrawn into the syringe plunger to remove the quantity of bone marrow desired. This procedure can be repeated as many times as is necessary to remove the desired amount of bone marrow which the surgeon believes is necessary for the procedure. When the instrument is to be withdrawn, the handle is grasped by the physician under the wings and pulled out of the incision area.

The principles, preferred embodiments and modes of operation of the present invention have been described in the foregoing specification However, the invention should not be construed as limited to the particular embodiments which have been described above. Instead, the embodiments described here should be regarded as illustrative rather than restrictive. Variations and changes may be made by others without departing from the scope of the present inventions defined by the following claims.

What we claim is:

1. A bone marrow aspiration instrument comprising: an elongated tubular cannula having an axially extending lumen therethrough and having distal and proximal ends; a handle body secured to the proximal end of said cannula, said handle body being provided with wing portions extending outwardly from to the axis of said cannula and defining a rounded cavity aligned with and open to the proximal end of said cannula, said handle further defining a stem positioned opposite said rounded cavity and extending away from said cavity and surrounding said cannula, each wing portion defining a lower outwardly curved lower surface and an upper planar surface, a stylet comprising a solid metal elongated shaft having a sharpened tip on one end and an anvil striking portion formed on its other end, said anvil portion being generally cylindrical with one end tapering to said shaft and the other end forming a planar striking surface, a stylet handle secured to said stylet on its proximal end, said stylet handle defining a rounded projection which seats in said cannula handle cavity and wing portions seated upon said cannula handle body wing portions upper planar surface, said elongated stylet shaft being slidably received within said cannula lumen, said stylet sharpened distal tip extending distally from the distal end of said cannula when said stylet is mounted in cannula lumen, locking means mounted in said cannula handle retaining said stylet in said cannula so that force may be applied to the striking surface of said elongated stylet positioned in said cavity without relative rotation between said elongated stylet and said elongated cannula, said handle body and said stylet handle when mounted together having a greater surface area located on one side of said cannula axis and a minor surface area located on an opposite side of said cannula axis so that both handle bodies are eccentrically mounted on the axis of said cannula.

2. A bone marrow aspiration instrument according to claim 1 wherein said stylet has a triangular planar surfaced tip.

3. A bone marrow aspiration instrument according to claim 1 wherein said stylet has a triangular concave surfaced tip.

4. A bone marrow aspiration instrument according to claim 1 wherein said cannula has scalloped sharpened end.

5. A bone marrow aspiration instrument according to claim 1 wherein a Luer lock is secured to said cannula handle communicating with said cannula lumen and extends upward into said cannula handle cavity.

6. A bone marrow aspiration instrument for use in collecting bone marrow from preselected portions of a human bone comprising:
   a. a cannula having a proximal end and a distal end with a lumen transversing said cannula from said proximal end to said distal end and a Luer lock secured to said cannula proximal end,
   b. a handle body eccentrically mounted to said cannula, said handle body defining gripping members of different lengths extending away from the axis of said cannula and a tapered stem which extends away from said handle body along a portion of said cannula length, said handle body further defining a seat for a stylet body;
   c. a solid stylet comprising a shaft with a proximal end forming an anvil striking surface and a distal end forming a sharpened tip, said stylet being insertable within said lumen of said cannula;
   d. a stylet handle secured to said stylet having a body with a protruding configuration allowing it to fit in said cannula handle body stylet seat and gripping members having a planar lower surface and length corresponding to the length of said cannula handle body gripping members which are seated on said cannula handle body gripping members, said stylet anvil striking surface extending above an upper surface of said stylet handle to provide a striking surface; and,
   e. means mounted to said stylet handle body coupling said stylet handle body to said Luer lock of said cannula.

7. A bone marrow aspiration instrument according to claim 6 wherein said cannula is coated with a surface lubricant coating.

8. A bone marrow aspiration instrument according to claim 7 wherein said lubricant coating comprising a group consisting of silicone, TEFLON and ground sapphire.

9. A bone marrow aspiration instrument according to claim 6 wherein said cannula surface is laser etched with bands to determine depth of penetration.

10. A bone marrow aspiration instrument according to claim 6 wherein said cannula handle body defines an upper surface with an arcuate seat formed therein to receive and hold said stylet body protruding configuration.

11. A bone marrow aspiration instrument according to claim 6 wherein said cannula and said stylet are constructed of stainless steel.

12. A bone marrow aspiration instrument for use in collecting bone marrow from preselected portions of a human bone comprising:
   a. a cannula having a proximal end and a distal end with a lumen transversing said cannula from said proximal end to said distal end and a mounting member mounted to said cannula,
   b. a handle body eccentrically mounted to said cannula, said handle body defining gripping sections in the form of wing members of different length extending away from the axis of said cannula and a stem which extends away from said handle body along a portion of said cannula length, said handle body further defining a recessed stylet handle seat, said wing members having an upper planar surface with at least one of said wing member planar surfaces being provided with locking means to prevent rotational movement between said cannula handle and a stylet handle;
   c. a solid stylet having a proximal end forming a striking surface and a distal end forming a sharpened tip removably inserted within said lumen of said cannula;
   d. a stylet handle secured to said stylet having a body with a protruding configuration allowing it to snugly fit in said cannula body recessed stylet handle seat and extending wing members having a lower planar surface which seats upon said cannula handle body upper planar wing surface; and,
   e. means attached to said stylet handle body to releasably couple said stylet handle body to said mounting member of said cannula handle body.

13. A bone marrow aspiration instrument according to claim 12 wherein said locking means is a detent adapted to receive a nipple on said stylet handle.

14. A bone marrow aspiration instrument according to claim 12 wherein said mounting means is a Luer lock.

15. A bone marrow aspiration instrument according to claim 12 wherein said stylet handle defines a chamber configured to receive a Luer lock and is provided with locking rods.

16. A bone marrow collecting instrument comprising:
   a stylet handle, said handle having an upper curved surface having an off-center radius to conform to the shape of a user's palm, said off-center radius being off-center with respect to a length of the handle, said handle also defining a lower surface defining an arcuate projection section and wing sections with lower planar surfaces; a stylet extending through said stylet handle a position at least slightly raised from said upper surface through said arcuate projection portion; a chamber formed in said stylet handle around said stylet forming a chamber to receive a leur lock from a cannula and locking means formed in said handle around said chamber to hold a leur lock in position; a cannula handle having extending wing portions with upper planar surfaces which engage said stylet handle wing sections lower planar surfaces, a stem and an arcuate recess to receive said first stylet handle section arcuate projecting portion, a cannula secured to said cannula handle, said cannula having a proximal end connected to a luer lock which extends into said cannula handle arcuate recess and said stylet handle recess when the respective handles are mounted to each other.

17. A bone marrow collecting instrument according to claim 16 wherein said cannula is coated with a surface lubricant coating.

18. A bone marrow collecting instrument according to claim 17 wherein said lubricant coating comprises a group consisting of silicone, TEFLON and ground sapphire.

19. A bone marrow collecting instrument according to claim 16 wherein said cannula surface is laser etched with bands to determine depth of penetration.

20. A bone marrow collecting instrument according to claim 16 wherein said stylet comprises an elongated shaft, one end of said shaft being formed to have a sharpened tip, the other end of said shaft tapering to a cylindrical striking anvil with a planar end surface, said planar end surface extending beyond an upper surface of said stylet handle body to form an accessible striking surface.

* * * * *